United States Patent
Parihar et al.

(10) Patent No.: US 10,052,087 B2
(45) Date of Patent: *Aug. 21, 2018

(54) CONTROL MODULE INTERFACE FOR MRI BIOPSY DEVICE

(71) Applicant: Devicor Medical Products, Inc., Cincinnati, OH (US)

(72) Inventors: Shailendra K. Parihar, Mason, OH (US); Todd M. Dahling, Loveland, OH (US); Patrick A. Mescher, Bellbrook, OH (US); John A. Hibner, Mason, OH (US); Trevor W. V. Speeg, Williamsburg, OH (US); Jessica P. Leimbach, Cincinnati, OH (US); Raj G. Raghavendran, Mason, OH (US); Gavin M. Monson, Oxford, OH (US)

(73) Assignee: Devicor Medical Products, Inc., Cincinnati, OH (US)

(*) Notice: Subject to any disclaimer, the term of this patent is extended or adjusted under 35 U.S.C. 154(b) by 312 days.

This patent is subject to a terminal disclaimer.

(21) Appl. No.: 14/845,443

(22) Filed: Sep. 4, 2015

(65) Prior Publication Data

US 2015/0374349 A1    Dec. 31, 2015

Related U.S. Application Data

(63) Continuation of application No. 14/092,263, filed on Nov. 27, 2013, now Pat. No. 9,134,388, which is a
(Continued)

(51) Int. Cl.
*A61B 5/00* (2006.01)
*A61B 10/04* (2006.01)
(Continued)

(52) U.S. Cl.
CPC ............. *A61B 10/04* (2013.01); *A61B 5/055* (2013.01); *A61B 10/0266* (2013.01);
(Continued)

(58) Field of Classification Search
CPC . A61B 5/055; A61B 10/0266; A61B 10/0275; A61B 10/0283; A61B 10/04;
(Continued)

(56) References Cited

U.S. PATENT DOCUMENTS 5,526,822 A    6/1996    Burbank et al.
6,086,544 A    7/2000    Hibner et al.
(Continued)

OTHER PUBLICATIONS

International Preliminary Report on Patentability dated Jun. 21, 2011 for Application No. PCT/US2009/067161, 9 pgs.
(Continued)

*Primary Examiner* — Max Hindenburg
(74) *Attorney, Agent, or Firm* — Frost Brown Todd LLC

(57) ABSTRACT

A biopsy system includes a biopsy device, a control module, a control module interface, at least one wireless data communication link, and an encoder. The biopsy device is operable to capture a tissue sample and includes a reusable portion and a disposable portion. The reusable portion includes an MR compatible motor. The disposable portion is adapted to be releasably joined with the reusable portion. The control module interface is configured to provide an interface between the control module and the reusable portion of the biopsy device. The at least one wireless data communication link includes a first data link configured to permit communication of data between the reusable portion of the biopsy device and the control module interface. The encoder is operationally coupled with the MR compatible motor.

21 Claims, 10 Drawing Sheets

Related U.S. Application Data continuation of application No. 13/674,371, filed on Nov. 12, 2012, now Pat. No. 8,617,084, which is a continuation of application No. 12/337,814, filed on Dec. 18, 2008, now Pat. No. 8,328,732.

(51) Int. Cl.
| | | |
|---|---|---|
| *A61B 10/02* | (2006.01) | |
| *A61B 5/055* | (2006.01) | |
| *G01R 33/28* | (2006.01) | |
| *A61B 17/34* | (2006.01) | |
| *A61B 17/00* | (2006.01) | |

(52) U.S. Cl.
CPC ...... *A61B 10/0275* (2013.01); *A61B 10/0283* (2013.01); *A61B 17/3403* (2013.01); *G01R 33/285* (2013.01); *A61B 2010/0208* (2013.01); *A61B 2010/045* (2013.01); *A61B 2017/00017* (2013.01); *A61B 2017/00199* (2013.01); *A61B 2017/00221* (2013.01); *A61B 2017/00911* (2013.01)

(58) Field of Classification Search
CPC ........... A61B 2017/00017; A61B 2017/00199; G01R 33/285
See application file for complete search history.

(56) References Cited

U.S. PATENT DOCUMENTS

| | | |
|---|---|---|
| 6,274,965 B1 | 8/2001 | Daum et al. |
| 6,626,849 B2 | 9/2003 | Huitema et al. |
| 6,904,305 B2 | 6/2005 | Tsekos |
| 7,442,171 B2 | 10/2008 | Stephens et al. |
| 7,507,210 B2 | 3/2009 | Hibner et al. |
| 7,846,109 B2 | 12/2010 | Parihar et al. |
| 7,914,464 B2 | 3/2011 | Burdorff et al. |
| 7,938,786 B2 | 5/2011 | Ritchie et al. |
| 8,251,916 B2 | 8/2012 | Speeg et al. |
| 8,328,732 B2 | 12/2012 | Parihar et al. |
| 8,460,206 B2 | 6/2013 | Parihar et al. |
| 8,617,084 B2 | 12/2013 | Parihar et al. |
| 8,622,927 B2 | 1/2014 | Parihar et al. |
| 8,702,623 B2 | 4/2014 | Parihar et al. |
| 8,932,233 B2 | 1/2015 | Haberstich et al. |
| 9,134,388 B2 | 9/2015 | Parihar et al. |
| 9,345,457 B2 | 5/2016 | Speeg et al. |
| 2010/0160819 A1 | 6/2010 | Parihar et al. |

OTHER PUBLICATIONS

International Search Report dated Aug. 20, 2010 for Application No. PCT/US2009/067161, 6 pgs.
U.S. Appl. No. 60/869,736, filed Dec. 13, 2006.
U.S. Appl. No. 60/874,792, filed Dec. 13, 2006.

CONTROL MODULE INTERFACE FOR MRI BIOPSY DEVICE

This application is a continuation of U.S. Pub. No. 2014/0088458, published Mar. 27, 2014, entitled "Control Module Interface for MRI Biopsy Device," which is a continuation of U.S. Pat. No. 8,617,084, issued Dec. 31, 2013, entitled "Control Module Interface for MRI Biopsy Device," which is a continuation of U.S. Pat. No. 8,328,732, issued Dec. 11, 2012, entitled "Control Module Interface for MRI Biopsy Device," the disclosure of which is incorporated by reference herein.

BACKGROUND

Biopsy samples have been obtained in a variety of ways in various medical procedures using a variety of devices. Biopsy devices may be used under stereotactic guidance, ultrasound guidance, MRI (magnetic resonance imaging) guidance, PEM (positron emission mammography) guidance, BSGI (breast-specific gamma imaging) guidance, MBI (molecular breast imaging) guidance, or otherwise. Merely exemplary biopsy devices are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pub. No. 2003/0109803, entitled "MRI Compatible Surgical Biopsy Device," published Jun. 12, 2003, now U.S. Pat. No. 6,626,849; U.S. Pub. No. 2007/0118048, entitled "Remote Thumbwheel for a Surgical Biopsy Device," published May 24, 2007, now U.S. Pat. No. 7,442,171; U.S. Pub. No. 2008/0214955, entitled "Presentation of Biopsy Sample by Biopsy Device," published Sep. 4, 2008; U.S. Provisional Patent Application Ser. No. 60/869,736, entitled "Biopsy System," filed Dec. 13, 2006; and U.S. Provisional Patent Application Ser. No. 60/874,792, entitled "Biopsy Sample Storage," filed Dec. 13, 2006. The disclosure of each of the above-cited U.S. patents, U.S. patent application Publications, and U.S. Provisional patent applications is incorporated by reference herein. While several systems and methods have been made and used for obtaining a biopsy sample, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Figure 1:
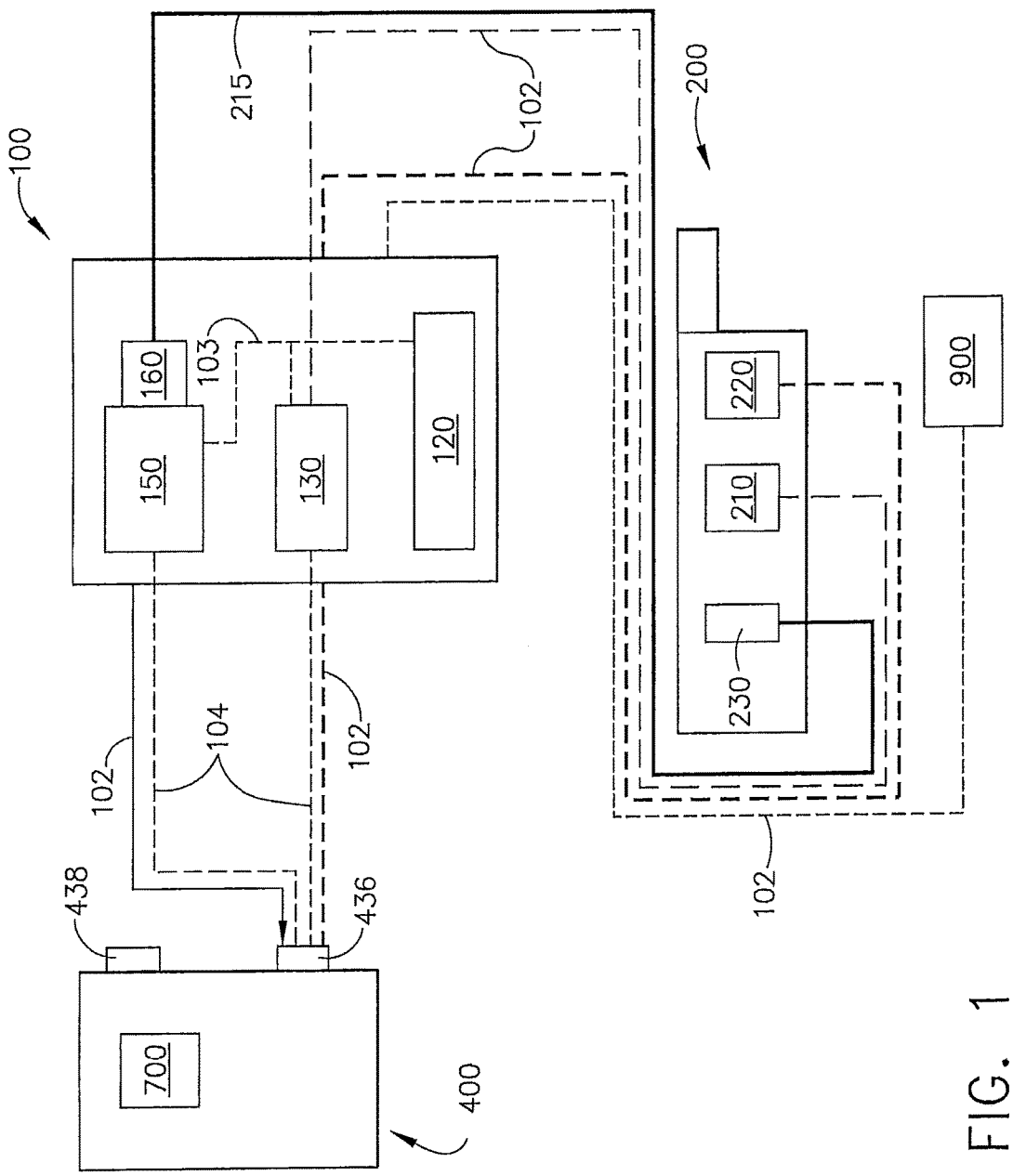
FIG. 1 depicts a schematic view of an exemplary biopsy system.

FIG. 1 depicts a schematic view of an exemplary biopsy system (2), which includes a control module interface (100), a biopsy device holster (200), an external input device (900), and a vacuum control module (400). As will be described in greater detail below, control module interface (100) may be configured to communicate with one or more external devices. In the illustrated version, control module interface (100) is in communication with biopsy device holster (200), input device (900), and vacuum control module (400). In this example, biopsy device holster (200) is a component of a biopsy device (250) that is configured to obtain a biopsy sample; and vacuum control module (400) is configured to work in conjunction with biopsy device (250) to obtain the sample. Control module interface (100) may be configured to be combined with a biopsy device holster (200) that is designed for use under stereotactic guidance, ultrasound guidance, MRI guidance, PEM guidance, BSGI guidance, MBI guidance, or another type of guidance; or any other suitable type of holster (200).

Figure 4:
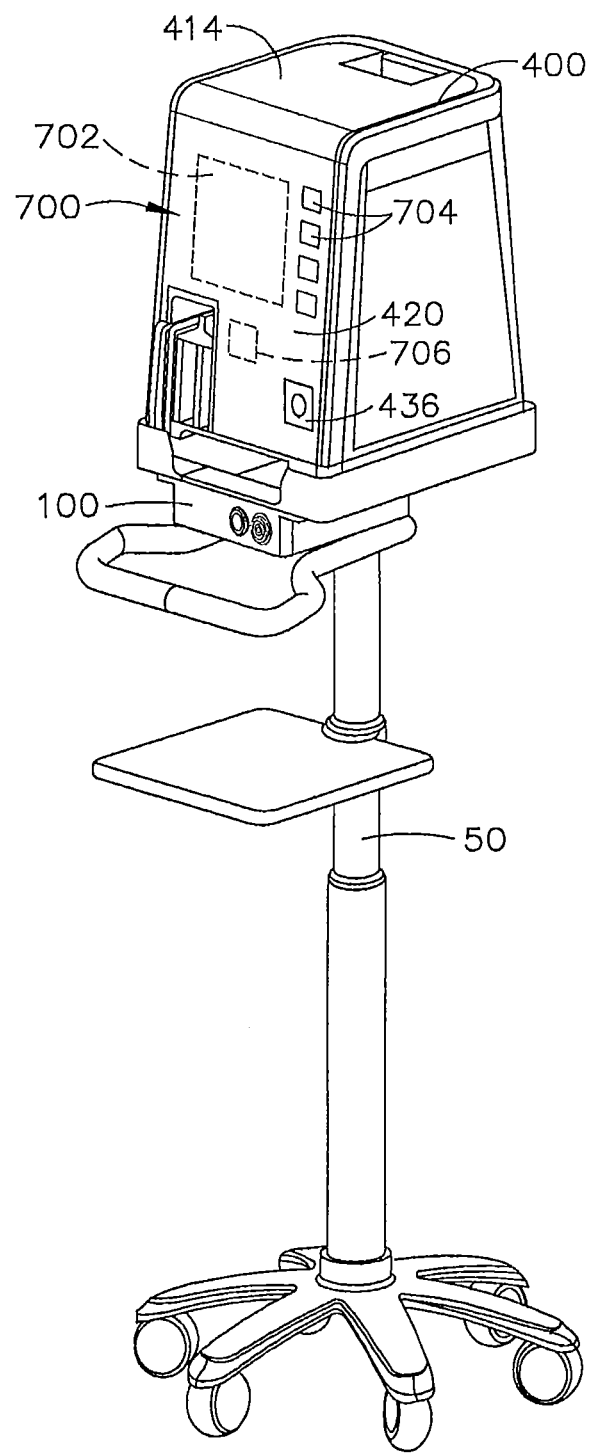
FIG. 4 depicts a perspective view of an exemplary control module interface mounted on a magnetic resonance imaging cart.

One or more of the components of biopsy system (2) may be configured to be mounted to, fastened to, or otherwise coupled with a cart (50) to increase portability. As shown in FIG. 4, control module interface (100) and vacuum control module (400) are mounted to cart (50) in this example (e.g., using clips, clamps, bolts, screws, complementary structural features for engagement, etc.). Portability of vacuum control module (400) and control module interface (100) may be desirable in magnetic resonance imaging (MRI) suite settings or in other settings. The use of electric motors, which may be incorporated within control module interface (100), may be restricted in magnetic environments, such as MRI suites. Therefore, mounting control module interface (100) and vacuum control module (400) may allow a user to easily position these components at an adequate distance (e.g., at least twelve feet) away from any magnetic equipment. Of course, a plurality of carts (50) may be used, as may portions of carts (50). Carts (50) may also be adjustable in any suitable fashion. Alternatively, control module interface (100) and/or vacuum control module (400) may be provided at any other suitable location(s) during use. Cart (50), vacuum control module (400), and/or control module interface (100) may also present one or more features to provide storage of excess cables, fluid communication tubes, etc.

I. Exemplary Biopsy Device

Figure 2:
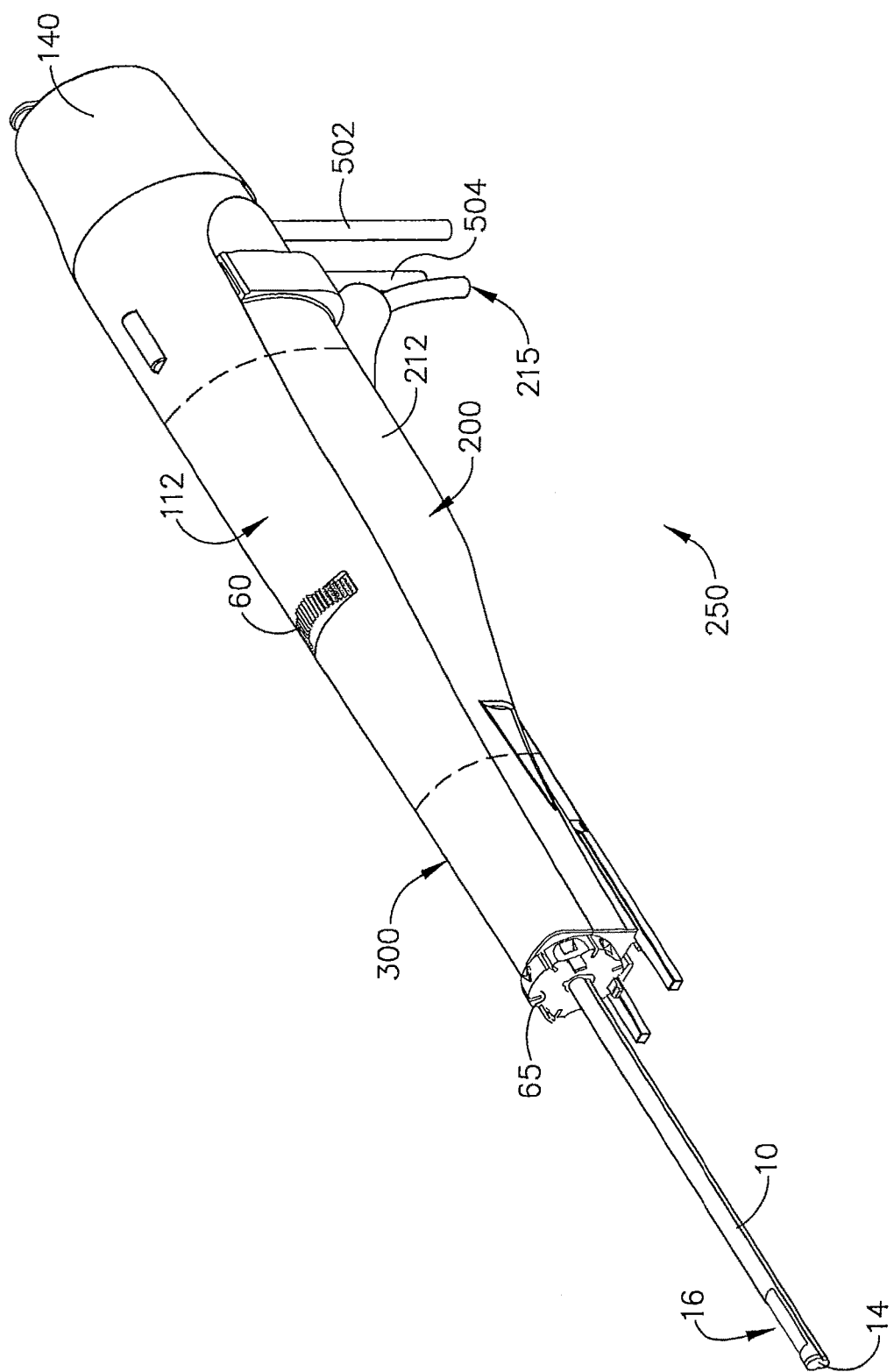
FIG. 2 depicts an exemplary biopsy device that may be used with the biopsy system of FIG. 1.
Figure 3:
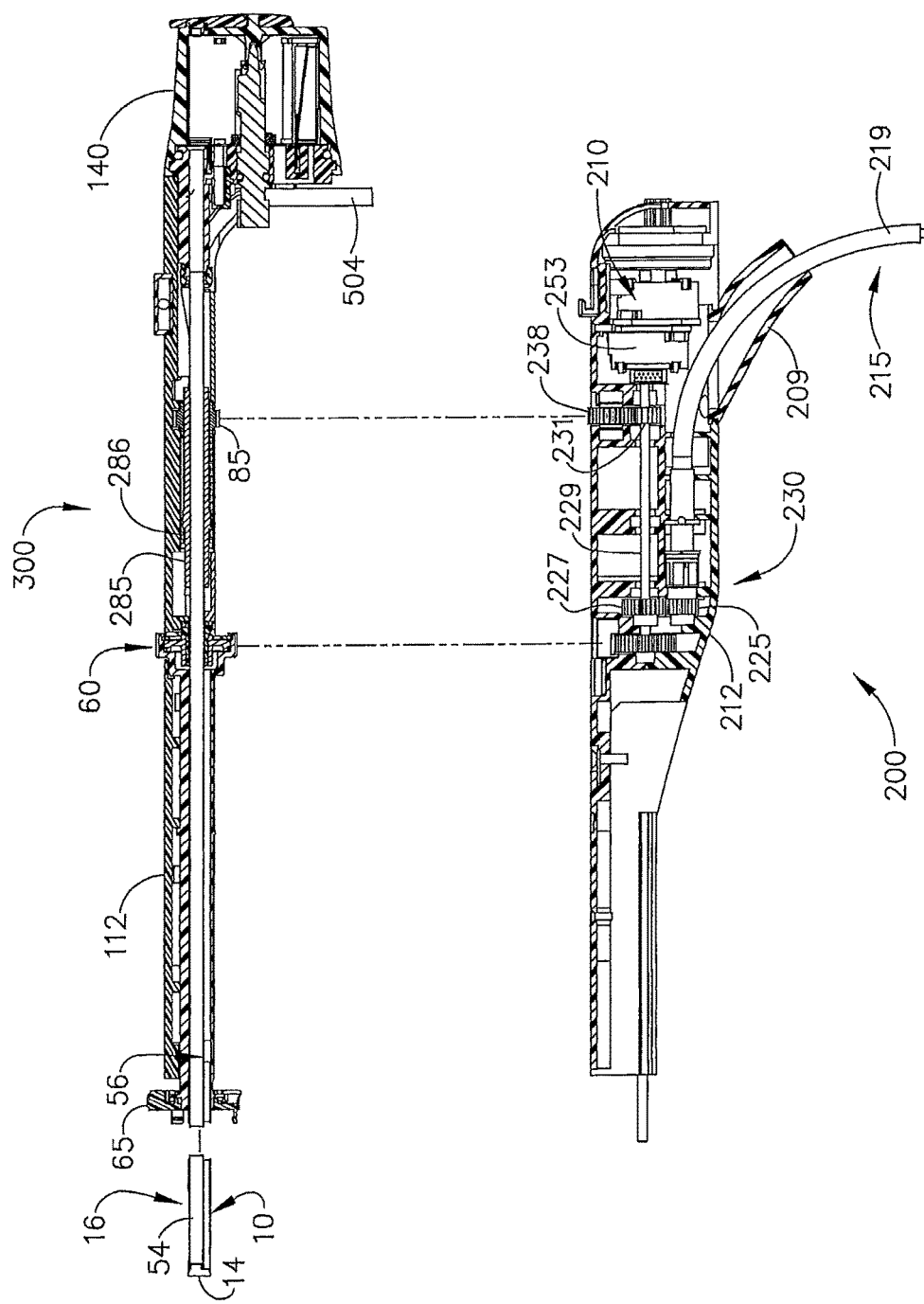
FIG. 3 depicts a side cross-sectional view of the biopsy device of FIG. 2, with a probe portion separated from a holster portion.

FIGS. 2-3 illustrate one merely exemplary biopsy device (250) that may be incorporated into biopsy system (2). As shown, biopsy device (250) comprises a probe (300) and a holster (200). Probe (300) and holster (200) are separable in this example, though such separability is not necessary. In some settings, biopsy device (250) may be manipulated and operated by a single hand of a user (e.g., using ultrasound guidance, etc.). However, it will be appreciated in view of the disclosure herein that biopsy device (250) may be configured to be mounted to a table, fixture, or other device, such as for use in a stereotactic or X-ray setting, an MRI setting, PEM setting, BSGI setting, MBI setting, or any other setting. By way of example only, holster (200) may be coupled with a targeting set, such as the targeting set disclosed in U.S. Non-Provisional patent application Ser. No. 12/337,872, entitled "MUTLI-ORIENTATION TARGETING SET FOR MRI BIOPSY DEVICE," filed on Dec. 18, 2008, issued as U.S. Pat. No. 8,460,206, the disclosure of which is incorporated by reference herein. Holster (200) may also be coupled with a targeting grid and cube as disclosed in U.S. Pub. No. 2007/0255170, entitled "BIOPSY CANNULA ADJUSTABLE DEPTH STOP," published Nov. 1, 2007, the disclosure of which is incorporated by reference herein.

In some versions, biopsy device (250) is configured and usable in accordance with the teachings of U.S. Non-Provisional patent application Ser. No. 12/337,874, entitled "MECHANICAL TISSUE SAMPLE HOLDER INDEXING DEVICE," filed on Dec. 18, 2008, issued as U.S. Pat. No. 8,622,927, the disclosure of which is incorporated by reference herein. In some other versions, biopsy device (250) is configured and usable in accordance with the teachings of U.S. Non-Provisional patent application Ser. No. 12/337,674, entitled "BIOPSY DEVICE WITH SLIDING CUTTER COVER," filed on Dec. 18, 2008, issued as U.S. Pat. No. 7,846,109, the disclosure of which is incorporated by reference herein. In other versions, biopsy device (250) is configured and usable in accordance with the teachings of U.S. Non-Provisional patent application Ser. No. 12/337,911, entitled "BIOPSY DEVICE WITH DISCRETE TISSUE CHAMBERS," filed on Dec. 18, 2008, published as U.S. Patent Pub. No. 2010/0160824, the disclosure of which is incorporated by reference herein. In still other versions, biopsy device (250) is configured and usable in accordance with the teachings of U.S. Non-Provisional patent application Ser. No. 12/337,942, entitled "TISSUE BIOPSY DEVICE WITH CENTRAL THUMB WHEEL," filed on Dec. 18, 2008, published as U.S. Patent Pub. No. 2010/0160819, the disclosure of which is incorporated by reference herein. Alternatively, biopsy device (250) may have a variety of other configurations and operational methods.

Biopsy device (250) may also be formed of materials that are safe in such environments. For instance, biopsy device (250) may be formed of materials permitting biopsy device (250) to be safely used in an MRI imaging environment, such that biopsy device (250) is "MR safe" or MR compatible, and such that MRI interference is minimized if not prevented. Of course, it will be appreciated in view of the disclosure herein that biopsy device (250) may be used in a variety of other settings and combinations.

A. Exemplary Probe

As shown in FIGS. 2-3, probe (300) of the present example comprises a needle portion (10), a body portion (112), and a tissue sample holder (140). Needle portion (10) has a blunt tip (14) and a transverse tissue receiving aperture (16) located proximally from the blunt tip (14). For instance, needle portion (10) may be introduced into a patient's breast through a separate cannula (not shown) that has a tissue piercing tip and a aperture configured to align with tissue receiving aperture (16) of needle portion (10). In alternate embodiments, blunt tip (14) may be replaced with a tissue piercing tip (not shown). Tissue piercing tip may be configured to penetrate tissue without requiring a high amount of force, and without requiring an opening to be preformed in the tissue prior to insertion of the needle portion (10). One suitable configuration for a tissue piercing tip is disclosed in U.S. Pub. No. 2008/0195066, entitled "Revolving Tissue Sample Holder For Biopsy Device," published Aug. 14, 2008, the disclosure of which is incorporated by reference herein. Tip (14) may also be RF capable or ultrasonic capable, to facilitate insertion of tip (14) in tissue, to facilitate hemostasis, etc. Other suitable configurations for a blunt tip (14) or tissue piercing tip will be apparent to those of ordinary skill in the art in view of the teachings herein.

Thumbwheels (60, 65) are secured relative to needle portion (10), and are operable to rotate needle portion (10). In particular, thumbwheels (60, 65) are operable to reorient the position of aperture (16) relative to the central axis defined by needle portion (10), such as to obtain various biopsy samples at different angular positions in a patient's breast without having to withdraw needle portion (10) from the patient's breast. An illustrative example of such rotation and acquisition of multiple tissue samples is disclosed in U.S. Pat. No. 5,526,822, the disclosure of which is incorporated by reference herein. Of course, some versions may provide rotatability of needle portion (10) in some other way, or not provide any rotatability of needle portion (10) at all. For instance, a thumbwheel (60, 65) may alternatively be located on either or both sides of biopsy device (250), at the rear of biopsy device (150), remote from biopsy device (250), and/or in any other suitable location(s). By way of example only, a thumbwheel (60, 65) may be configured, located, and/or operated in accordance with any of the teachings of U.S. Non-Provisional patent application Ser. No. 12/337,942, entitled "TISSUE BIOPSY DEVICE WITH CENTRAL THUMBWHEEL," filed on Dec. 18, 2008, published as U.S. Patent Pub. No. 2010/0160819, the disclosure of which is incorporated by reference herein.

A hollow tubular cutter (54) is disposed within needle portion (10), and is operable to sever tissue protruding through tissue receiving aperture (16) when needle portion (10) is inserted in a patient. Furthermore, cutter (54) defines a cutter lumen (56), through which severed tissue samples may be communicated proximally to reach tissue sample holder (140). Tissue samples may be communicated proximally through cutter lumen (56) under the influence of a vacuum and/or pressurized air or using any other suitable techniques. At least a portion of tissue sample holder (140) is removable from probe body portion (112) in this example, to permit retrieval of tissue samples therefrom.

As shown in FIG. 3, an overmold (285) is provided about cutter (54). Overmold (285) has an externally threaded portion and an external hex portion, and is secured unitarily to cutter (54). A gear (85) is provided about the hex portion of overmold (285), and is operable to rotate unitarily with overmold (285) while also being able to translate longitudinally relative to overmold (285). For instance, gear (85)

may have an internal hex profile that complements an external hex profile of overmold (285). Alternatively, a key-keyway relationship or other type of structural relationship may be provided. A nut (286) is secured relative to body portion (112), and has an internal threaded region through which externally threaded portion of overmold (285) passes. In particular, as overmold (285) rotates, engagement between threading of overmold (285) and threading of nut (286) results in translational movement of overmold (285) relative to nut (286) (and, hence, relative to body portion (112)). It should therefore be understood that rotation of gear (85) can cause simultaneous rotation and longitudinal translation of overmold (285) relative to body portion (112); and hence, simultaneous rotation and longitudinal translation of cutter (54) relative to body portion (112). A portion of gear (85) is exposed through body portion (112) of probe (300). Gear (85) may thus itself be rotated by gear (238), as will be explained in greater detail below, when probe (300) is coupled with holster (200).

A pair of tubes (502, 504) are coupled with probe (300), and are operable to provide fluid communication (e.g., vacuum, saline, pressurized air, venting, etc.) between probe (300) and vacuum control module (400) and/or any other device or system. For instance, tube (502) may provide fluid communication with a portion of the interior of needle portion (10) that is exterior to cutter (54). Tube (504) may provide fluid communication with cutter lumen (56) via tissue sample holder (140). Suitable structures and techniques for providing such fluid communication, as well as other suitable features of or for probe (300), are disclosed in U.S. Non-Provisional patent application Ser. No. 12/337, 942, entitled "TISSUE BIOPSY DEVICE WITH CENTRAL THUMBWHEEL," filed on Dec. 18, 2008, the disclosure of which is incorporated by reference herein. Other suitable structures and techniques for providing such fluid communication as well as other suitable features of or for probe (300), are disclosed in U.S. Pub. No. 2008/0195066, entitled "Revolving Tissue Sample Holder For Biopsy Device," published Aug. 14, 2008, the disclosure of which is incorporated by reference herein. Alternatively, fluid communication may be provided in any other suitable fashion, to the extent that any fluid communication is provided at all; and probe (300) may have any other suitable structures, features, components, and configurations, as desired.

B. Exemplary Holster

Figure 11:
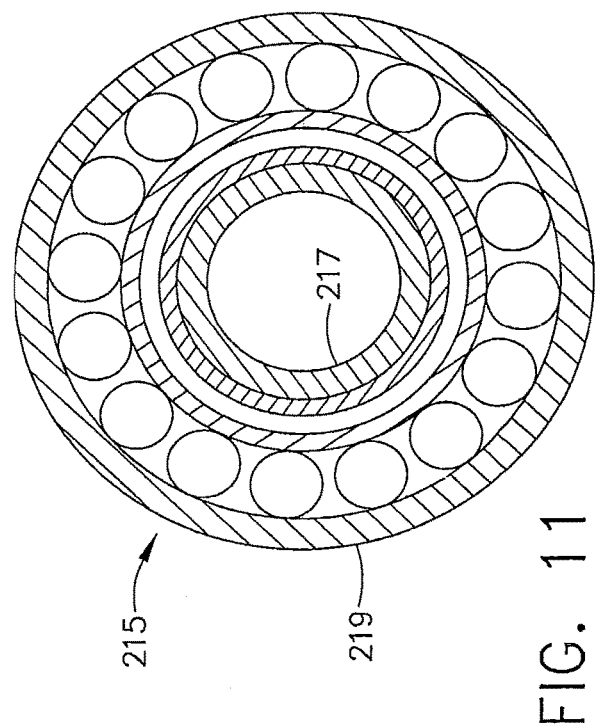
FIG. 11 depicts a transverse cross-sectional view of an exemplary mechanical cable that may be used with the biopsy system of FIG. 1.

As shown in FIG. 1, holster (200) is in communication with control module interface (100), input device (900) (via control module interface (100)) and vacuum control module (400) (via control module interface (100)). As shown in FIGS. 2-3, holster (200) of the present example comprises a body portion (212) and a mechanical cable assembly (215) extending therefrom. A strain relief boot (209) is provided at the interface of body portion (212) and mechanical cable assembly (215). As shown in FIG. 11, mechanical cable assembly (215) comprises a flexible cable (217) and a sheath (219). Flexible cable (217) may be similar to a speedometer cable, such that rotation of cable (217) is communicated along the length of cable (217) without significantly twisting up or binding cable (217). Cable assembly (215), including any or all of its components, may be formed of MR compatible materials, such that cable assembly (215) is MR safe. As will be described in greater detail below, cable (217) is configured to receive rotational motion from shaft connector (164) of control module interface (100), and transmit such rotational motion to gear (225) of holster (200).

Cable (217) of the present example is of sufficient length to permit biopsy device (250) to be operated at least approximately 10 to 12 feet away from control module interface (100) and vacuum control module (400). For instance, such a distance may allow biopsy device (250) to be successfully operated within the magnetic field of an MRI suite, while reducing exposure or preventing exposure of control module interface (100) and vacuum control module (400) to such a magnetic field.

Holster (200) includes a cutter driving mechanism (230), which is configured to ultimately transfer rotational motion of cable (217) into simultaneous rotation and translation of cutter (54). Cutter driving mechanism (230) comprises several gears (225, 227, 231, 238) and a shaft (229). As noted above, gear (225) is coupled with cable (217), and is configured to receive rotational motion from cable (217). Gear (225) may be engaged with and transfer rotational motion to another gear (227), which may transfer the rotational motion to yet another gear (231) via shaft (229). Gear (231) may in turn transfer the rotational motion to another gear (238). A portion of gear (238) may be exposed through body portion (212) of holster (200), permitting gear (238) to mesh with gear (85) when probe (300) is coupled with holster (200). As noted above, gear (238) may thus transfer rotational motion to gear (85). It should therefore be understood in view of the teachings herein that rotation of cable (217) by shaft connector (164) may ultimately be converted into simultaneous rotation and translation of cutter (54), by virtue of the configurations and relationships between cable (217), gears (225, 227, 231, 238, 85), shaft (229), overmold (285), nut (286), body portion (112), and cutter (54). Of course, a variety of other structures, configurations, components, devices, and techniques may be used to provide rotational and/or translational movement of cutter (54).

Holster (200) of the present example further comprises a piezo motor (210) and an encoder (220). Piezo motor (210) may comprise a USR30-B4 motor by Shinsei Corporation of Tokyo, Japan, or any other suitable motor. Alternatively, a non-piezo motor may be used, if desired. Encoder (220) may comprise a R22i encoder by Renco Encoders, Inc. of Goleta, Calif., or any other suitable encoder. Encoder (220) may be operationally coupled with one or more of piezo motor (210), cutter driver mechanism (230), or any other component of holster (200). Piezo motor (210) may be operable to rotate a portion of tissue sample holder (140) (e.g., to successively index discrete tissue sample chambers to cutter lumen (56) for collection of discrete tissue samples). Alternatively, piezo motor (210) may be used for other purposes, or may me simply omitted altogether. Encoder (220) may be configured to gather and transmit information indicative of the rotational and/or translational position of cutter (54). In addition or in the alternative, encoder (220) may be configured to gather and transmit information indicative of the rotational position of a portion of tissue sample holder (140) (e.g., indicative of how many tissue sample chambers in tissue sample holder have been indexed to cutter lumen (56), etc.). Alternatively, encoder (220) may be used to gather any other type of information, or may be simply omitted altogether. To the extent that an encoder (220) is used, encoder (220) may be provided in any suitable location, such as holster (200), probe (300), somewhere between biopsy device (250) and control module interface (100), within control module interface (100), or any other suitable location (e.g., to minimize MR interference or for other purposes).

Other suitable features of or for holster (200) are disclosed in U.S. Non-Provisional patent application Ser. No.

12/337,942, entitled "TISSUE BIOPSY DEVICE WITH CENTRAL THUMBWHEEL," filed on Dec. 18, 2008, the disclosure of which is incorporated by reference herein. Still other suitable features of or for holster (200) are disclosed in U.S. Pub. No. 2008/0195066, entitled "Revolving Tissue Sample Holder For Biopsy Device," published Aug. 14, 2008, the disclosure of which is incorporated by reference herein. Alternatively, holster (200) may have any other suitable structures, features, components, and configurations, as desired. Similarly, holster (200) may be operated in accordance with any of the teachings of U.S. Non-Provisional patent application Ser. No. 12/337,942, entitled "TISSUE BIOPSY DEVICE WITH CENTRAL THUMBWHEEL," filed on Dec. 18, 2008, the disclosure of which is incorporated by reference herein; and/or U.S. Pub. No. 2008/0195066, entitled "Revolving Tissue Sample Holder For Biopsy Device," published Aug. 14, 2008, the disclosure of which is incorporated by reference herein.

II. Exemplary Input Device

As shown in FIG. 1, input device (900) is in direct communication with control module interface (100) via a data communication link (102). Input device (900) is also indirectly in communication with holster (200) and vacuum control module (400) via control module interface (100). Input device (900) may comprise a keypad, touch screen, keyboard, foot switch, or any other suitable device. Input device (900) may be configured to receive input (e.g., commands and signals, etc.) from a user in order to allow a user to operate one or more components of biopsy system (2), including holster (200) and/or vacuum control module (400). Input received via input device (900) may then be communicated to the appropriate component via a data communications link (102). Data communication links (102) may comprise a communication cable, an electrical cable, a wireless communication link, or any other suitable method or device. Input device (900) may be used in conjunction with or as an alternative to user interface (700) on vacuum control module (400) and/or in conjunction with or as an alternative to any user interface that may be presented by biopsy device (250). The connections and communication between input device (900) and control module interface (100) will be discussed in more detail below.

III. Exemplary Vacuum Control Module

As shown in FIG. 4, the vacuum control module (400) of the present example comprises an outer casing (414) and a user interface (700). In some versions, vacuum control module (400) may further comprise a set of operational electronics (not shown) as an alternative to or in addition to the set of operational electronics housed within control module interface (100). The operational electronics may be configured to control one or more components of biopsy device system (2). Of course, operational electronics in vacuum control module (400) are not required. Outer casing (414) includes a face portion (420), behind which resides a display screen (702), capacitive switches (704), and a speaker (706). Face portion (420) is configured such that display screen (702) can be viewed therethrough; such that capacitive switches (704) may be activated therethrough; and such that sounds coming from speaker (706) can be heard therethrough. Display screen (702), switches (704), and speaker (706) may be regarded as collectively forming user interface (700). Vacuum control module (400) may be tilted to permit easier viewing of screen (702). Alternatively, a screen (702) may be external to vacuum control module (400) permitting an operator to adjust the external screen to an appropriate position to facilitate viewing of and interaction with the screen (702). Similar to input device (900), user interface (700) may be configured to receive input (e.g., commands, signals, etc.) from a user, thereby allowing a user to control one or more components of biopsy device system (2). Input from a user may be communicated from vacuum control module (400) to control module interface (100) or holster (200) via a data communication link (102). User interface (700) may be used in conjunction with or as an alternative to external input device (900).

In the illustrated version, vacuum control module (400) also comprises a front connector (436) and a rear connector (438). Of course, any suitable number of connectors (436, 438) in any suitable configuration may be used. By way of example only, multiple connectors may be used to communicate power, electrical signals, etc. to or from vacuum control module (400). It will be appreciated by those of ordinary skill in the art in view of the teachings herein that front connector (436) and/or rear connector (438) may be used to couple vacuum control module (400) with a variety of other devices, including but not limited to an interface, such as control module interface (100), a local or remote desktop or laptop computer, the internet, a local area network, any other network, a storage device, or a device associated with one or more particular imaging modalities (e.g., a pod or cart associated with Magnetic Resonance Imaging, etc.).

Front connector (436) and rear connector (438) may permit data and/or commands to be communicated between vacuum control module (400) and an external device, such as control module interface (100), holster (200) and input device (900). By way of example only, front connector (436) may provide power to either or both motors (150, 210). Alternatively, front connector (436) may provide power (e.g., phased power) to motor (150); while rear connector (438) provides power to piezo motor (210) (e.g., through piezo controller (130), etc.). Of course, those roles of connectors (436, 438) could be reversed, as desired. Cutter position feedback from encoder (220) may also be communicated back to vacuum control module (400) via front connector (436) or rear connector (438). Similarly, to the extent that another encoder (not shown) is provided to obtain information on the rotational position of a rotational component of tissue sample holder (140), such position feedback may be communicated back to vacuum control module (400) via front connector (436) or rear connector (438). Other ways in which front connector (436) and rear connector (438) may be used will be apparent to those of ordinary skill in the art in view of the teachings herein.

Vacuum control module (400) may be configured and/or operated in accordance with any of the teachings of U.S. Pub. No. 2008/0195066, entitled "Revolving Tissue Sample Holder For Biopsy Device," published Aug. 14, 2008, the disclosure of which is incorporated by reference herein.

IV. Exemplary Control Module Interface

Figure 5:
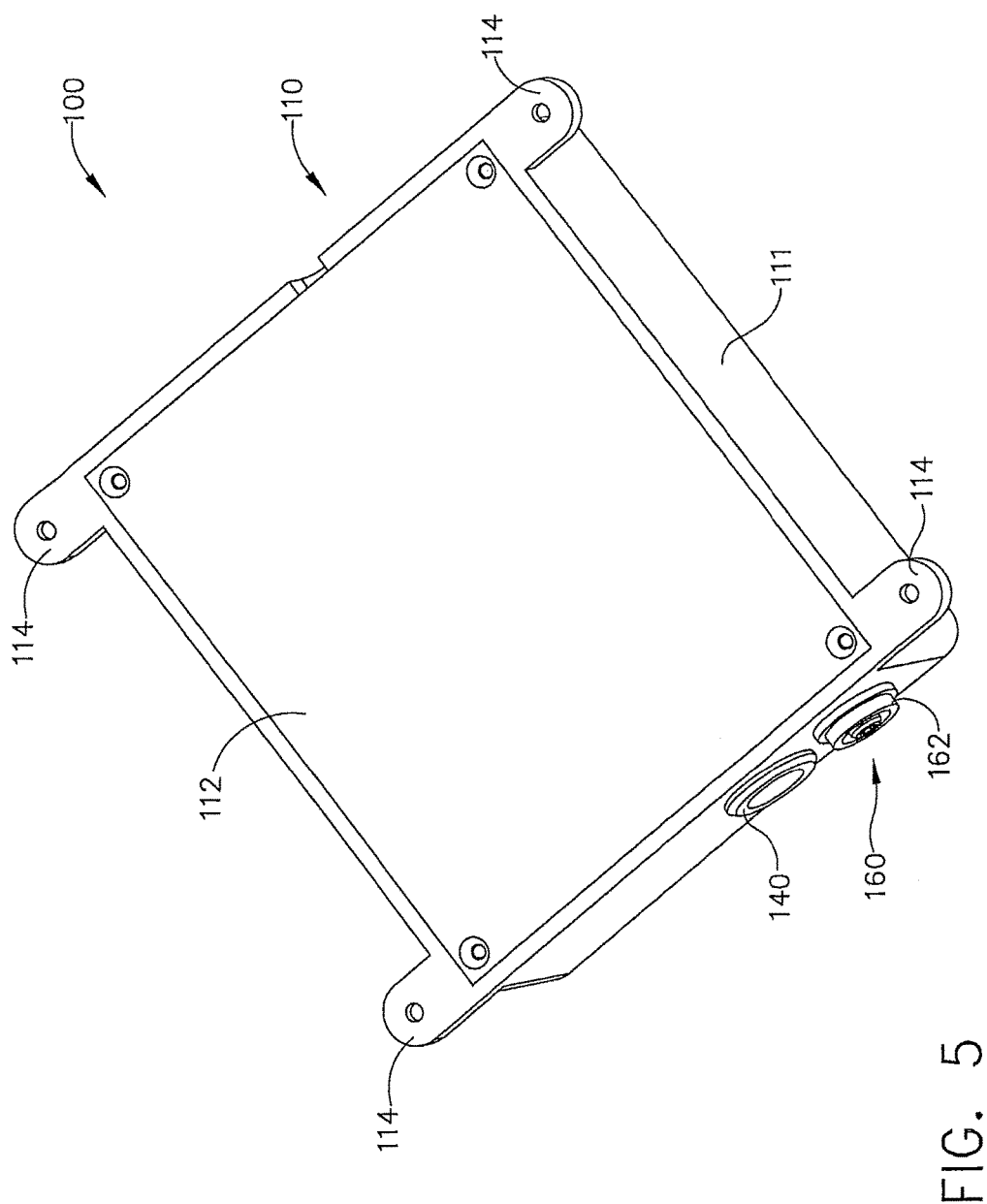
FIG. 5 depicts a perspective view of the control module of FIG. 1.
Figure 6:
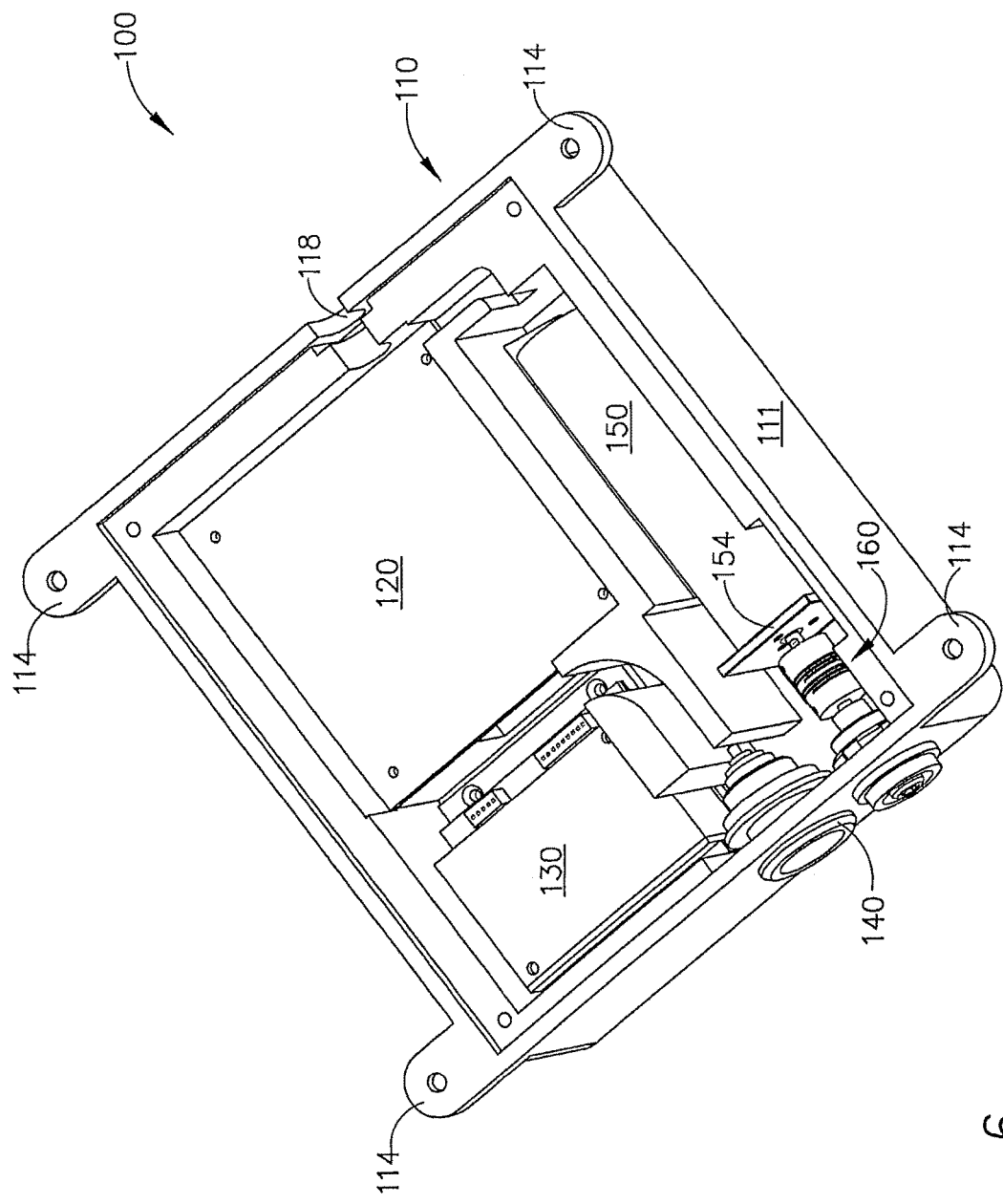
FIG. 6 depicts a perspective view of the control module of FIG. 1 with the top plate of the casing removed.

As illustrated by FIG. 1, control module interface (100) is configured to serve as an electrical and mechanical interface between holster (200), input device (900), and vacuum control module (400). As noted above, in certain environments, it may be beneficial to contain magnetically sensitive components, including but not limited to electric motors and operational electronics, such as controllers, in a separate unit, such as control module interface (100). This modularization may allow a user to remotely position these components to avoid interference with other pieces of equipment. As shown in FIGS. 5-6, control module interface (100) of the present example comprises a cabinet (110), a microcontroller circuit board (120), a piezo motor controller (130), an electrical connector (140), a motor (150), and a shaft connection assembly (160).

In the present example, control module interface (100) is provided as a simple retrofit to a preexisting vacuum control module (400). For instance, a user may already have a vacuum control module (400) that is constructed in accordance with the teachings of U.S. Pub. No. 2008/0195066, entitled "Revolving Tissue Sample Holder For Biopsy Device," published Aug. 14, 2008, the disclosure of which is incorporated by reference herein. The user may easily couple control module interface (100) with vacuum control module (400), and control module interface (100) may cooperate with vacuum control module (400) with relative ease. For instance, control module interface (100) may be coupled with front connector (436) of vacuum control module (400), and vacuum control module (400) may be operable in the same way it would be having a biopsy device coupled directly to front connector (436) (e.g., without a control module interface (100) being positioned between the biopsy device and the vacuum control module (400). Alternatively, the presence of control module interface (100) may provide additional functionalities to vacuum control module (400) and/or disable certain functionalities of vacuum control module (400). If desired, various ways in which vacuum control module (400) may become aware of the coupling of control module interface (100) will be apparent to those of ordinary skill in the art in view of the teachings herein. Alternatively, vacuum control module (400) may be kept oblivious to the coupling of control module interface (100). Vacuum control module (400) may attach to the top of control module interface (100) (or vice-versa; within control module interface (100) (or vice-versa); or elsewhere. Vacuum control module (400) and/or control module interface (100) may also be mobile (e.g., of a size and weight such that a single person may carry either or both with relative ease).

A. Exemplary Cabinet

In the illustrated version, cabinet (110) comprises a lower body (111), a removable lid (112), a plurality of mounting extensions (114), an electrical connector opening (116), a shaft connection assembly opening (117) and a rear opening (118). Removable lid (112) is releasably engaged with lower body (111). Removable lid (112) may be attached to lower body (111) using one or more suitable fasteners, including but not limited to screws, pins, bolts, hinges, etc. As shown in FIGS. 3-5, cabinet (110) includes four mounting extensions (114) positioned on each of the four corners of lower body (111). Mounting extensions (114) may be configured to allow cabinet (110) to be mounted to cart (50), as shown in FIG. 2, or any other suitable structure. Of course, mounting extensions (114) may alternatively be varied in any suitable way, as desired, if not omitted altogether.

In this embodiment, electrical connector opening (116) and shaft connection assembly opening (117) are positioned along a front-facing portion of lower body (111). In addition, electrical connector opening (116) is configured to accommodate electrical connector (140), while shaft connection assembly opening (117) is configured to accommodate shaft connection plug (162) of shaft connection assembly (160). Rear opening (118) is positioned along a rear-facing portion of lower body (111) and is configured to provide access to the interior cavity of cabinet (110) for additional wiring, cables, or other connection or power components. Other suitable configurations and positions for electrical connector opening (116), shaft connection assembly opening (117) and rear opening (118) will be apparent to those of ordinary skill in the art in view of the teachings herein.

Figure 7:
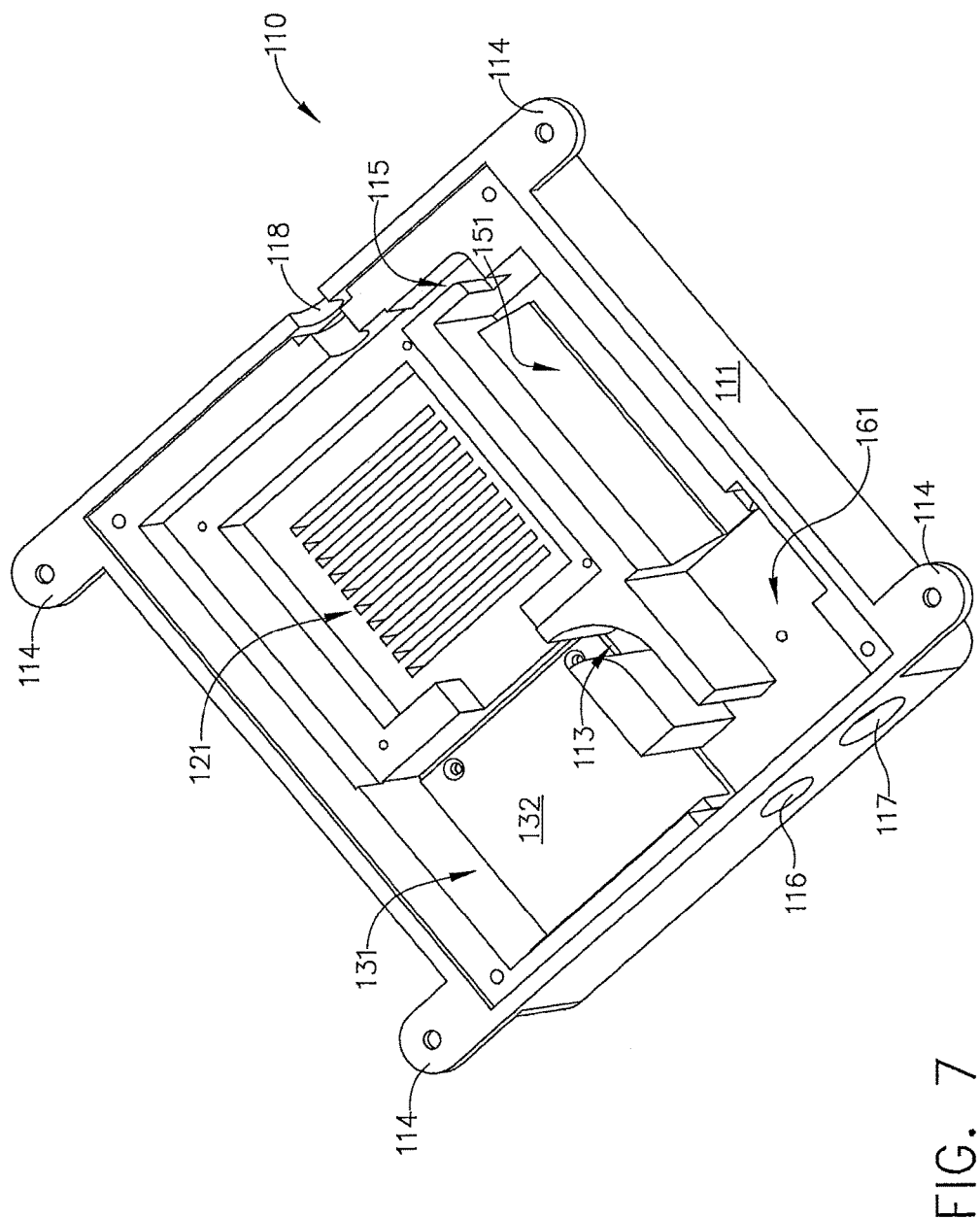
FIG. 7 depicts perspective view of an exemplary casing and exemplary piezo motor mounting of the control module interface of FIG. 5 with the other components removed.

As shown in FIGS. 6-7, cabinet (110) comprises a plurality of compartments (121, 131, 151, 161) configured to individually house various components, including microcontroller circuit board (120), piezo motor controller (130), electrical connector (140), motor (150), and shaft connection assembly (160). In the illustrated version, compartment (121) houses microcontroller circuit board (120) and includes slits in the bottom face of lower body (111) to provide ventilation. Compartment (131) is configured to house piezo motor controller (130). Mounting plate (132) is configured to fit within compartment (131) and secure piezo motor controller (130). As shown, motor (150) is housed within compartment (151), while compartment (161) is adjacent to shaft connection assembly opening (117) and houses shaft connection assembly (160). Motor mounting plate (154) is configured to secure motor (150) within compartment (151). Of course, cabinet (110) may be configured to house any suitable number of components in any suitable configuration. Components, such as microcontroller circuit board (120) and piezo motor controller (130) may be secured to lower body (111) using screws, bolts, pins, adhesive, mounting plates, or any other suitable structures or techniques.

Lower body (111) may also include channels formed within lower body (111), such as channels (113, 115), configured to allow the components to be connected. For example, channel (113) provides a pathway for a connection between piezo motor controller (130) and electrical connector (140). Similarly, channel (115) provides a pathway for a connection between microcontroller circuit board (120) and motor (150). Any suitable number of channels in any suitable configuration may be incorporated within lower body (111).

B. Exemplary Operational Electronics

Control module interface (100) of the present example comprises operational electronics, including microcontroller circuit board (120) and piezo motor controller (130) operable to control various components of biopsy system (2). The operational electronics contained in control module interface (100) may be incorporated in biopsy device system (2) as an alternative to or in addition to operational electronics housed within vacuum control module (400) or elsewhere. Microcontroller circuit board (120) and piezo motor controller (130) may be configured to control and/or receive input from one or more external devices connected to control module interface (100), including but not limited to holster (200), input device (900), and vacuum control module (400). In particular, among other operations, microcontroller circuit board (120) is operable to control motor (150) housed within cabinet (110) and piezo motor controller (130) is operable to control piezo motor (210) housed within holster (200).

As discussed above, a user may input commands or signals to operate one or more components of biopsy system (2) via input device (900) or user interface (700). In this example, such input is communicated to control module interface (100) via a data communication link (102), and, more particularly, microcontroller circuit board (120) or piezo motor controller (130). That input may be processed by microcontroller circuit board (120) and/or piezo motor controller (130), along with other input from various signals and sensors (not shown), to control motor (150) and/or piezo motor (210) in accordance with the user's instructions.

By way of example only, microcontroller circuit board (120) and/or piezo motor controller (130) may be configured in accordance with any of the relevant teachings of U.S. Pub. No. 2008/0195066, entitled "Revolving Tissue Sample Holder For Biopsy Device," published Aug. 14, 2008, the disclosure of which is incorporated by reference herein. Alternatively, any other suitable configurations may be used.

C. Exemplary Motors

In the illustrated version, motor (150) is configured to drive cutter driver mechanism (230) incorporated within holster (202). Alternatively, motor (150) may be configured to drive additional or alternative components within holster (202). As shown, motor (150) comprises a rotatable output shaft (152). Output shaft (152) is remotely connected to cutter drive mechanism (230) via shaft connection assembly (160) and mechanical cable (215), as noted above. By way of example only, as also noted above, mechanical cable (215) may comprise a flexible shaft cable, such as a speedometer cable. Of course, other suitable cables, as well as other suitable devices or techniques to communicate rotation from motor (150) to cutter drive mechanism (230) will be apparent to those of ordinary skill in the art based on the teachings herein. The connection between motor (150) and cutter drive mechanism (230) will be discussed in greater detail below. Motor (150) may incorporate brushed or brushless technology. Motor (150) may also use electrical or optical commutation, although this is not required. For instance, motor (150) may comprise a 24 VDC motor (e.g., 60 W brush motor, EC22 50 W BLDC motor, a 60 W BDC motor, 8 W BLDC motor, etc.), or any other suitable type of motor. Motor (150) may also be coupled with an encoder (not shown) within control module interface (100), such as to gather information on rotational positioning and/or speed of motor (150), etc.

D. Exemplary Communication Between Components

In the present example, control module interface (100) is configured to house certain mechanical and electrical components such that control module interface (100) may be positioned remotely from one or more components of biopsy system (2) (e.g., remotely from biopsy device (250). The remote positioning is possible because control module interface (100) is configured to remain in electrical and/or mechanical communication with each of the other components of biopsy system (2). As illustrated in FIG. 1, control module interface is in mechanical and electrical communication with holster (200), input device (900), and vacuum control module (400).

In the present example, data communication links (102) are configured to allow data, including but not limited to commands, control signals, sensor signals, etc., to be communicated between control module interface (100) and the other components of biopsy device system (2). Data communication links (102) may comprise a communication cable, an electrical cable, a wireless communication link, or any other suitable structure or means of communication. In embodiments where data communication links (102) comprise a physical cable (such as a communication or electrical cable), data communication links (102) may be of sufficient length to allow the user to place control module interface (100) sufficiently far away from any magnetic resonance imaging equipment to avoid interference resulting from any magnetic field (e.g., at 1 Tesla, etc.) created by the MR imaging equipment. For instance, a suitable distance may be in the range of between about 10 feet and about 12 feet, or any other suitable distance. Physical cables for data and/or electrical communication may or may not also be coupled with mechanical cable assembly (e.g., secured external to or internal to sheath (219), etc.).

Data communication links (102) may be connected to control module interface (100) and its components via electrical connector (140). Control module interface (100) serves as an intermediate processor for communication between holster (200), input device (900), and vacuum control module (400). For example, in the illustrated embodiment, if a user attempts to operate holster (200) by entering in a command via user interface (700) on vacuum control module (400), the command is communicated from interface (700) to control module interface (100) via a data communication link (102), processed by microcontroller circuit board (120) and/or piezo motor controller (130), and, subsequently communicated to holster (200) via a data communication link (102). Similarly, a command entered into input device (900) is communicated from input device (900) to control module interface (100) via a data communication link (102), processed by microcontroller circuit board (120) or piezo motor control (130) and, subsequently communicated to holster (200) or vacuum control module (400) as appropriate via a data communication link (102). In addition, feedback, such as signals generated by encoder (220), may also be communicated to control module interface (100) via a data communication link (102), processed, and, ultimately, communicated to vacuum control module (400) via a data communication link (102) to generate a display on user interface (700) or for some other operational use.

Control module interface (100) may further comprise an internal data communication link (103) configured to allow communication between microcontroller circuit board (120), piezo motor controller (130), and motor (150). In particular, commands to operate motor (150) may be processed by microcontroller circuit board (120) and subsequently communicated to motor (150) via communication link (103). Such commands may be influenced at least in part by cutter position data communicated by encoder (220). Piezo motor controller (130) may or may not be in communication with each other, as desired.

An extra encoder (not shown) may be included in holster (200), for sensing the rotational position of a rotatable component of tissue sample holder (140). Data from such an encoder may be communicated back to circuit board (120) and/or piezo motor controller (130), to at least partially influence operation of motor (210). By way of example only, piezo motor controller (130) may drive motor (210) by transmitting a bi-phase sinusoidal waveform, with phase being locked to the rotational frequency. Of course, any other suitable type of waveform or other type of control signal may be used. It should also be understood that any other suitable type of motor controller may be used, in addition to or in lieu of a piezo motor controller (130). The inventors thus contemplate a variety of types of motors and motor controllers as being usable, in addition to or in lieu of a piezo motor (210) and a piezo motor controller (130).

Control module interface (100) may also be configured to receive power from an external device. In the illustrated version, power communication links (104) communicate power from vacuum control module (400) to control module interface (100). Power communication links (104) may be connected to control module interface (100) via electrical connector (140), through rear opening (118), or through any other suitable connection. In particular, power to operate motor (150) is communicated directly from vacuum control module (400). In the present example, power to operate piezo motor (210) is communicated from vacuum control module (400) through piezo motor controller (130) and, ultimately, to piezo motor (210) via an additional power communication link (not shown) between control module interface (100) and piezo motor (210). Alternatively, power may be communicated to piezo motor (210) via communication link (102) between control module interface (100) and piezo motor (210).

In the present example, control module interface (100) is also in mechanical communication with holster (200). More precisely, motor (150) is mechanically connected to cutter drive mechanism (230) in holster (200) via a mechanical cable (215). As shown, and as described above, mechanical cable (215) is configured to translate rotational motion generated by motor (150) to cutter drive mechanism (230). Mechanical cable (215) may comprise a flexible shaft cable, such as a speedometer cable, or any other suitable device or technique. Mechanical cable (215) may be of sufficient length to allow the user to place control module interface (100) sufficiently far away from any magnetic resonance imaging equipment to avoid interference resulting from any magnetic fields created by the imaging equipment. Motor (150) is configured to rotate output shaft (152). Output shaft is connected to mechanical cable (215) via shaft connection assembly (160).

Figure 8:
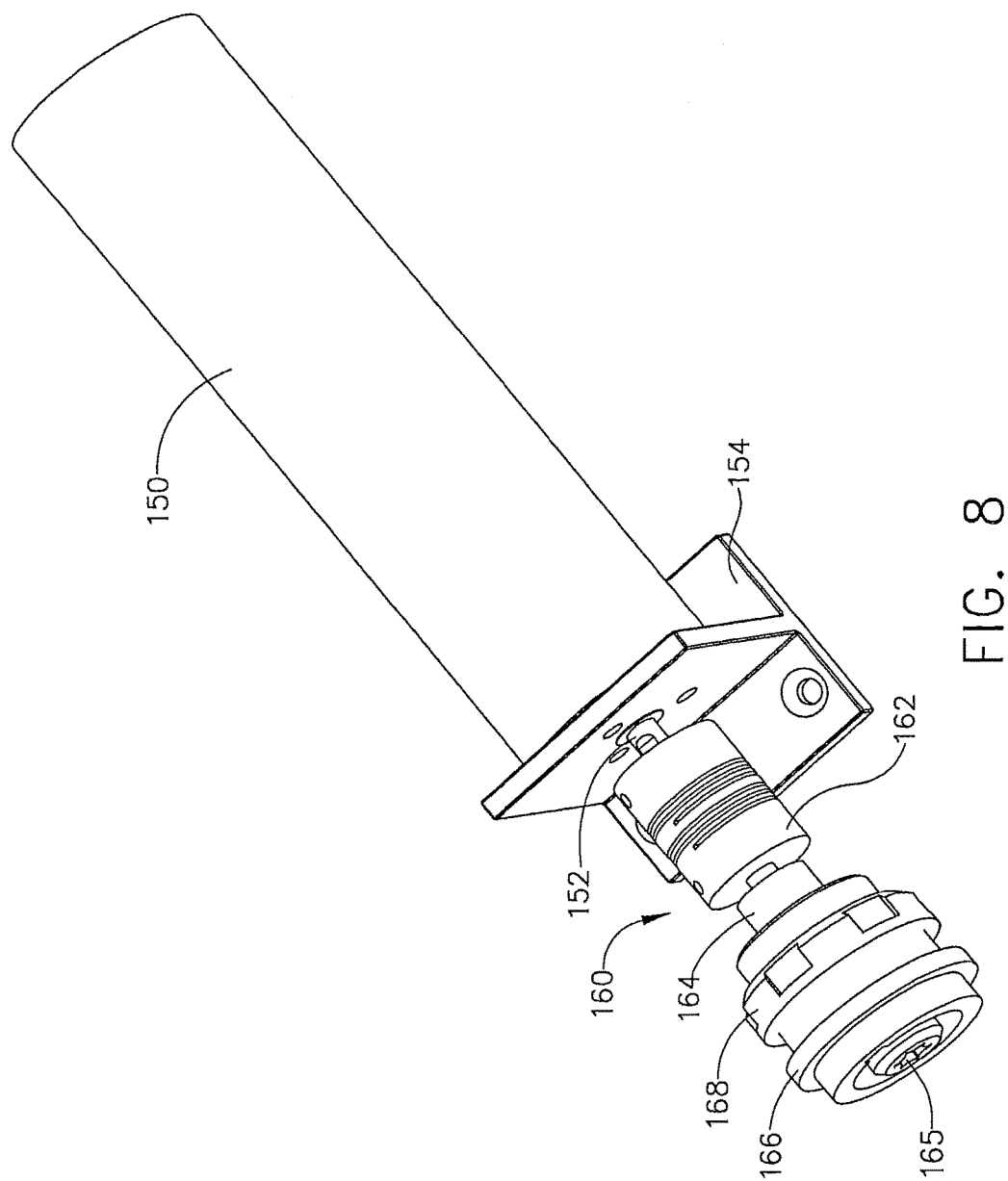
FIG. 8 depicts a perspective view of an exemplary cutter motor assembly of the control module of FIG. 1.
Figure 9:
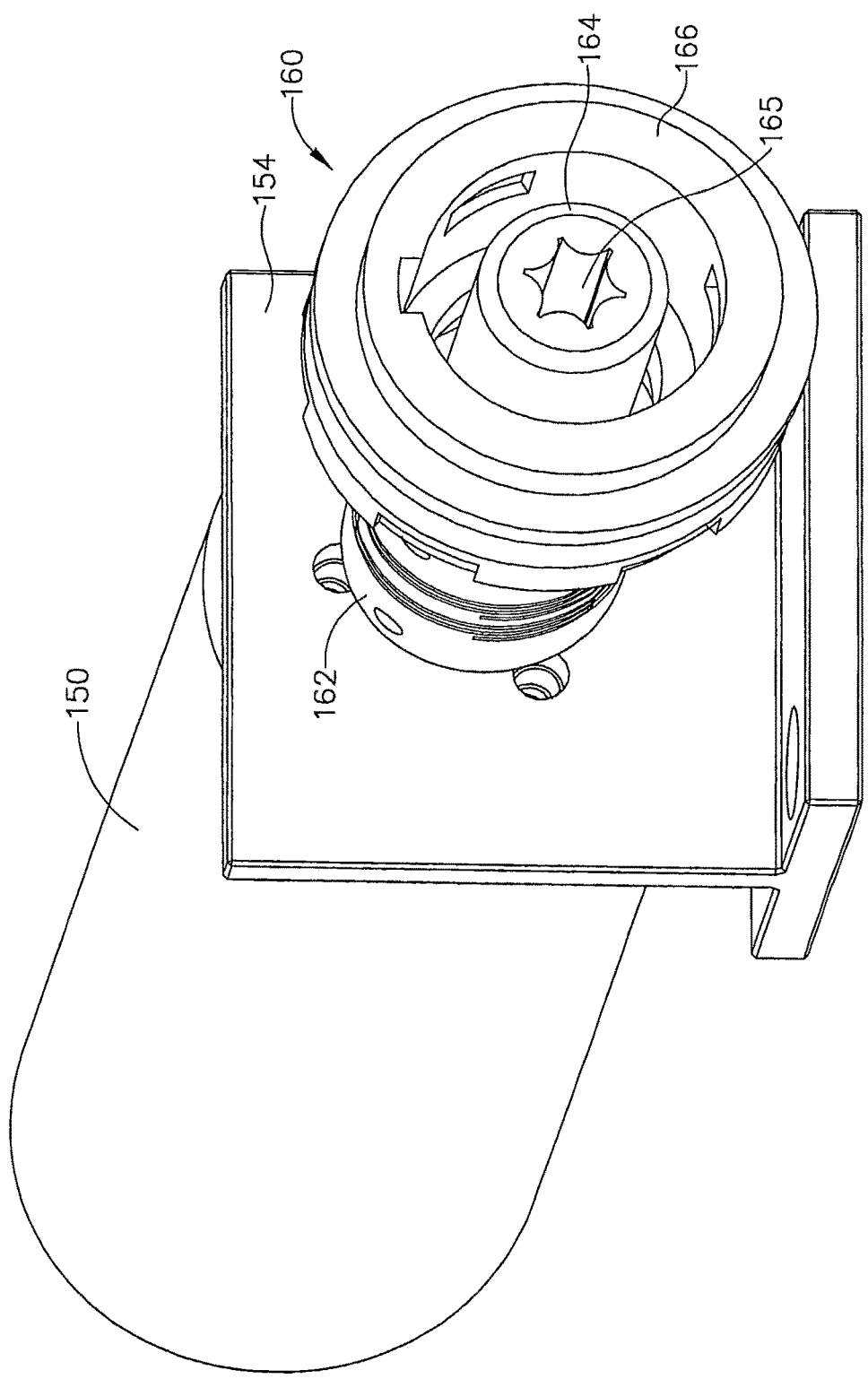
FIG. 9 depicts a detailed partial perspective view of the cutter motor assembly of FIG. 8.
Figure 10:
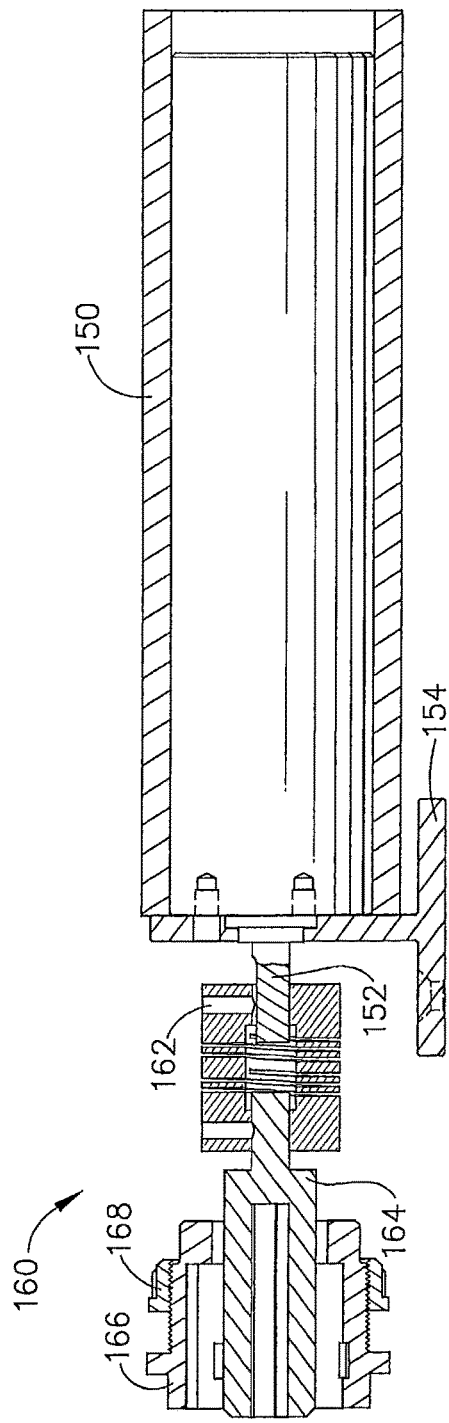
FIG. 10 depicts a lateral cross-sectional view of the cutter motor assembly of FIG. 8, taken along a longitudinal plane.

As shown in FIGS. 8-10, shaft connection assembly (160) comprises a flexible coupling (162), shaft connector (164), shaft plug (166), and shaft locking nut (168). Flexible coupling (162) is configured to engage output shaft (152) and shaft connector (164) such that output shaft (152) and shaft connector (164) rotate unitarily. Shaft connector (164) comprises an opening (165) configured to receive an end of mechanical cable (215) (in particular, the end of flexible cable (217)). In the illustrated version, opening (165) is star-shaped, however other suitable shapes or configurations will be apparent to those of ordinary skill in the art based on the teachings herein. One end of mechanical cable (215) is inserted into shaft connector (164) such that mechanical cable (215), output shaft (152), and shaft connector (164) rotate unitarily. Once mechanical cable (215) is inserted into shaft connector (164) and connected to cutter driver mechanism (230) at the opposite end, mechanical cable (215) is capable of communicating rotation generated by motor (150) to cutter driver mechanism (230). Shaft plug (166) is configured to occupy shaft connection assembly opening (117), and shaft locking nut (168) is configured to secure shaft plug (166) within shaft connection assembly opening (117).

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A biopsy system comprising:
   (a) a biopsy device, wherein the biopsy device is operable to capture a tissue sample, wherein at least a portion of the biopsy device comprises an encoder;
   (b) a motor, wherein the motor is configured to operate the biopsy device;
   (c) a controller, wherein the controller is configured to control the motor based on output from the encoder; and
   (d) a wireless data communication link configured to permit communication of data between the control module and the encoder.

2. The biopsy system of claim 1, wherein the biopsy device further comprises:
   (i) a needle portion,
   (ii) a cutter translatable relative to the needle portion, wherein the cutter is configured to sever tissue received by the needle portion to provide tissue samples
   (iii) a cutter drive operable to translate and rotate the cutter relative to the needle portion, and
   (iv) a tissue sample holder operable to receive tissue samples severed by the cutter.

3. The biopsy system of claim 2, wherein the motor is configured to operate the cutter drive.

4. The biopsy system of claim 2, wherein the tissue sample holder is rotatable.

5. The biopsy system of claim 4, wherein the motor is configured to rotate the tissue sample holder.

6. The biopsy system of claim 5, wherein the encoder is configured to provide a rotational position of a portion of the tissue sample holder, wherein the controller is configured to provide power to the motor to adjust the rotational position of the portion of the tissue sample holder based on feedback from the encoder.

7. The biopsy system of claim 2, wherein the encoder is configured to provide a rotational position of a portion of the cutter drive, wherein the controller is configured to provide power to the motor to adjust the rotational position of the cutter drive based on feedback from the encoder.

8. The biopsy system of claim 1 further comprising a control module interface, wherein the control module interface is in communication with the controller.

9. The biopsy system of claim 8, wherein the control module interface is configured to act as an intermediate data processor for the controller.

10. The biopsy system of claim 1 further comprising a vacuum control module, wherein the vacuum control module is operable to provide vacuum to the biopsy device.

11. The biopsy system of claim 1 further comprising a mechanical communication link couplable between the motor and the biopsy device.

12. The biopsy system of claim 11, wherein the biopsy device comprises a cutter, wherein the mechanical communication link is configured to permit communication of rotation motion from the motor to the cutter, wherein the encoder is configured to provide data based on movement of the cutter to the controller, wherein the controller is configured to adjust power supplied to the motor in response to data received from the encoder based on movement of the cutter.

13. The biopsy system of claim 1, wherein the biopsy device is configured to house the motor.

14. The biopsy system of claim 1, wherein the motor comprises a piezo motor.

15. A biopsy system comprising:
   (a) a biopsy device comprising:
      (i) a needle portion,
      (ii) a cutter translatable relative to the needle portion, wherein the cutter is configured to sever tissue received by the needle portion to provide tissue samples, and
      (iii) a tissue sample holder operable to receive tissue samples severed by the cutter;

(b) a motor configured to operate the cutter of the biopsy device;
(c) a controller configured to control the motor;
(d) an encoder, wherein the encoder is associated with at least a portion of the biopsy device;
(e) a wireless data communication link configured to permit communication of data between the controller and the encoder.

16. The biopsy system of claim 15, further comprising a mechanical data communication link, wherein the mechanical data communication link is configured to communicate rotation of the motor to the cutter of the biopsy device, wherein the encoder is configured to provide cutter position data to the controller, wherein the controller is configured to adjust operation of the motor based on the cutter position data.

17. The biopsy system of claim 16, wherein the mechanical data communication link communicates between the controller and the biopsy device.

18. A biopsy system comprising:
(a) a biopsy device, wherein the biopsy device is operable to capture a tissue sample, wherein the biopsy device includes a motor, a first encoder, and a second encoder, wherein the first encoder is associated with the motor, wherein the second encoder is associated with a drive mechanism disposed within the biopsy device;
(c) a controller, wherein the controller is configured to operate the motor of the biopsy device;
(d) a wireless data communication link configured to permit communication of signals between the controller and the first and second encoders of the biopsy device.

19. The biopsy system of claim 16, wherein the controller is positioned remotely relative to the biopsy device.

20. The biopsy system of claim 16, wherein the controller is configured to compare signals received from the first encoder with signals received from the second encoder to adjust operation of the motor and thereby synchronize the signals received from the first encoder and the second encoder.

21. The biopsy system of claim 1, further comprising:
a housing containing the motor and the controller; and
a drive cable adapted to couple between the motor and the biopsy device to drive the cutter to cut the tissue.

* * * * *